US007074966B2

(12) United States Patent
Hauer et al.

(10) Patent No.: US 7,074,966 B2
(45) Date of Patent: Jul. 11, 2006

(54) PROCESS FOR PRODUCTION OF R-PHENYLACETYLCARBINOL BY AN ENZYMATIC PROCESS IN A TWO-PHASE SYSTEM

(75) Inventors: Bernhard Hauer, Fussgönheim (DE); Michael Breuer, Limburgerhof (DE); Peter Rogers, Northwood (AU); Vanessa Sandford, Pacific Palms (AU); Bettina Rosche, Randwick (AU)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/488,202

(22) PCT Filed: Sep. 1, 2002

(86) PCT No.: PCT/EP02/09723

§ 371 (c)(1), (2), (4) Date: Mar. 1, 2004

(87) PCT Pub. No.: WO03/020942

PCT Pub. Date: Mar. 13, 2003

(65) Prior Publication Data

US 2004/0241816 A1  Dec. 2, 2004

(30) Foreign Application Priority Data

Sep. 1, 2001  (DE) ............... 101 42 574

(51) Int. Cl.
*C07C 45/72* (2006.01)
*C07C 211/00* (2006.01)

(52) U.S. Cl. ............. 568/311; 568/312; 568/336; 564/305

(58) Field of Classification Search ........... 568/311, 568/312, 336; 564/305
See application file for complete search history.

(56) References Cited

U.S. PATENT DOCUMENTS 5,079,145 A * 1/1992 Seely et al. ............... 435/34

6,004,789 A  12/1999 Bruhn et al. ............... 435/189

FOREIGN PATENT DOCUMENTS

| DE | 548459 | 4/1932 |
|---|---|---|
| WO | WO 90/04639 | 5/1990 |
| WO | WO 96/37620 | 11/1996 |
| WO | WO 99/09195 | 2/1999 |
| WO | WO 99/63103 | 12/1999 |

OTHER PUBLICATIONS

Nikolova, P., et al., "Production of Phenylacetyl Carbinol by Biotransformation Using Baker's Yeast in Two-Phase Systems," *Progress in Biotechnology*, 8:675-680 (1992).

Nikolova, P., et al., "Whole Cell Yeast Biotransformations in Two-Phase Systems: Effect of Solvent on Product Formation and Cell Structure," *Journal of Industrial Microbilogy*, 10(3-4):169-177 (1992).

Oliver, Alison L., et al., "Factors Affecting the Productiono f L-Phenylacetylcarbinol by Yeast: A Case Study," *Advances in Microbial Physiology*, 41:1-45 (1999).

Ward, Owen P., et al., "Enzymatic Asymmetric Synthesis by Decarboxylases," *Current Opinion in Biotechnology*, 11(6):520-526 (2000).

Dornemann, S., et al., "Stereospecific Formation of R-Aromatic Acyloins by Zymomonas Mobilis Pyruvate Decarboxylase," *Journal of the Chemical Society, Perkin Transactions*, 1(5):425-430 (1996).

Rosche, Bettina, et al., "Enhanced Production of R-Phenylacetylcarbinol (R-PAC) Through Enzymatic Biotransformation," *Journal of Molecular Catalysis B: Enzymatic*, 10(20):109-115 (2002).

Shin, Hyoun S., et al., Production of L-Phenylacetylcarbinol (L-PAC) from Benzaldehyde Using Partially Purified Pyruvate Decarboxylase (PDC), *Biotechnology and Bioengineering*, 49(1):52-62 (1996).

* cited by examiner

Primary Examiner—Sikarl A. Witherspoon
(74) Attorney, Agent, or Firm—Connolly Bove Lodge & Hutz

(57) ABSTRACT

This application relates to a new process for the production of R-phenylacetylcarbinol by an enzymatic process in a liquid two-phase system.

18 Claims, 7 Drawing Sheets

PROCESS FOR PRODUCTION OF R-PHENYLACETYLCARBINOL BY AN ENZYMATIC PROCESS IN A TWO-PHASE SYSTEM

This application is the national stage of PCT/EP02/09723, filed Sep. 1, 2002, and published as WO 03/020942 on Mar. 13, 2003.

FIELD OF THE INVENTION

This application relates to a new process for the production of R-phenylacetylcarbinol by an enzymatic process in a liquid two-phase system.

DESCRIPTION OF THE BACKGROUND

R-phenylacetylcarbinol (R-PAC) is a precursor for the chemical synthesis of ephedrine and pseudoephedrine. A method for the production of R-PAC by fermenting yeast (*Saccharomyces cerevisiae*) in the presence of benzaldehyde and molasses was established in the last century already (Hildebrandt & Klavehn 1932, DE-PS 548 459).

It also known for quite some time that the catalyst responsible for the synthesis of R-PAC in micro-organisms is the enzyme pyruvate decarboxylase (PDC). The enzyme converts the stereo-selective carboligation of a C2 moiety stemming from pyruvic acid and benzaldehyde. The catalyst also performs the carboligation of a number of other carbonyl-compound. With certain enzymes e.g. from *Zymomonas mobilis* also acetaldehyde instead of pyruvic acid can be used as substrate for the process.

Pyruvate decarboxylase (PDC) was identified and characterised in different organisms besides *Saccharomyces cerevisiae* and *Zymomonas mobilis*. The enzymatic synthesis of R-phenylacetylcarbinol by PDC has been described so far only in an aqueous one-phase-system. There is no information that pyruvate decarboxylase is also active in an organic solvent or in an emulsion of organic solvents and water.

In WO 96/37620 a process for producing acyloins, especially R-phenylacetylcarbinol from benzaldehyde and acetaldehyde or pyruvate in presence of pyruvate decarboxylase from *Zymomonas mobilis* is disclosed.

SUMMARY OF THE INVENTION

One embodiment of the invention is directed to processes for producing phenylacetylcarbinols of formula (I) comprising reacting, in a liquid two-phase system with at least one aqueous phase, acetaldehyde or pyruvate and an aromatic aldehyde of formula (II) in the presence of a pyruvate decarboxylase, to form a phenylacetylcarbinol. Preferably one liquid phase of said liquid two-phase system is an aqueous phase and another liquid phase of the liquid two-phase system is an organic phase, immiscible with the aqueous phase. Preferable liquid phases include, but are not limited to liquids selected from the group consisting of alkanes, alkanols, ethers, hydrophilic polymeric compounds, polyethylenglycols, alkanols, alkanols from $C_4$ to $C_{10}$, butanol, pentanol, hexanol, heptanol,octanol, nonanol, decanol and combinations and mixtures thereof.

The two liquid phases may be mechanically agitating wherein agitating comprises stirring or shaking such that the two phases are maintained as two discrete phases or, alternatively, stirring or shaking such that the two phases do not exist as separate phases but form an emulsion. The pyruvate decarboxylase may be derived from a microorganism of the genus *Zymomonas* such as *Z. mobilis*, or a microorganism of *C. utilis*. Preferably the acetaledyde is metered during the reaction such that acetaldehyde is at a concentration of between 20 and 50 mMol/L in the aqueous phase.

Another embodiment of the invention is directed to utilizing phenylacetylcarbinol produced by the process of the invention as a precursor in the formation of ephedrine or pseudoephedrine.

Another embodiment of the invention is directed to phenylacetylcarbinol produced by the process of the invention.

Another embodiment of the invention is directed to ephedrine or pseudoephedrine produced from phenylacetylcarbinol made by a process of the invention.

Other embodiments and advantages of the invention are set forth in part in the description, which follows, and in part, may be obvious from this description, or may be learned from the practice of the invention.

DESCRIPTION OF THE INVENTION

Subject of the present invention is a process for the bio-transformation of benzaldehyde and pyruvate with pyruvate decarboxylase (PDC) in a liquid two-phase-system, that means the reaction takes place in two liquid phases which are not miscible within each other. One of the liquid phases is an aqueous phase, the second liquid phase is a phase which is not miscible with the aqueous phase and which is not one of the reactants.

The second liquid phase can be varied broadly. Suitable for the second phase are alkanes, alkanols, ethers. Suitable are also hydrophilic polymeric compounds such as polyethylenglycols which build a second liquid phase if they get in contact with an aqueous phase.

Preferred embodiments for the second phase are alkanols, especially the alkanols from $C_4$ to $C_{10}$, i.e. butanol, pentanol, hexanol, heptanol, octanol, nonanol, decanol or mixtures of these alcohols. Among these the n-alkanols are preferred. Especially preferred are n-octanol and n-nonanol.

Depending on the agitation/mixing of the reaction medium two different two-phase systems were evaluated: two-phase separated mode refers to a two phase system where both phases are stirred as two discrete phases. This embodiment of the invention is called the "two-phase separated mode".

Another embodiment of the invention is the "two-phase mixed mode". By strong mixing of the two phases especially by strong stirring or shaking, the two phases do not exist any more as separate phases but form an emulsion. This embodiment is called the "two phase mixed mode".

Another embodiment of the invention is a process for the production of phenylacetylcarbinols of the general formula (I)

where R stands for H, F, Cl or B,

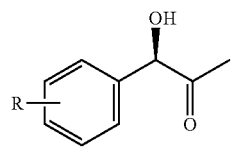

from Acetaldehyde and Aromatic aldehydes of the general formula (II)

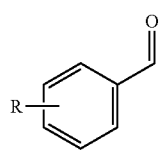

in the presence of a pyruvate decarboxylase, characterized in that the reaction takes place in a liquid two-phase system with at least one aqueous phase.

Further embodiments of the invention are disclosed in the claims and the examples.

The following examples illustrate embodiments of the invention, but should not be viewed as limiting the scope of the invention.

EXAMPLE 1

Selection of Organic Phase

PDC activity was measured in the presence of different organic solvents.

Figure 1A:
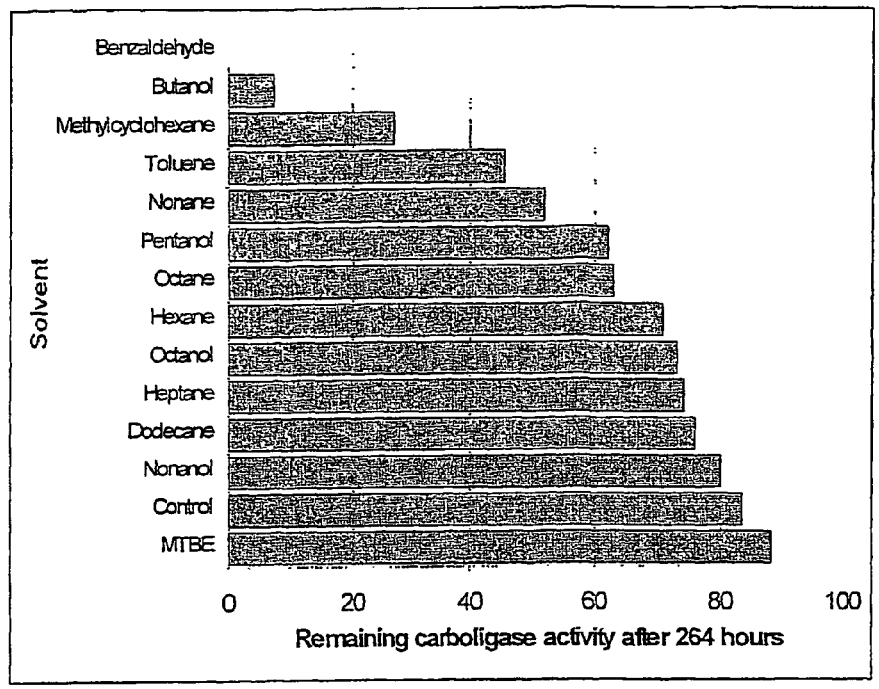
FIG. 1. Comparison of all solvents evaluated in an embodiment of the invention.

A comparison of all solvents evaluated is shown in FIG. 1A. The remaining carboligase activity after 264 hours of exposure is compared to a control with no solvent. The solvent MTBE has a positive effect on enzyme stability.

The enzyme exhibited enhanced stability to methyl-tert-butyl-ether (MTBE) in comparison to a control exposed to no solvent. MTBE may interact favorably with the active center or on the surface of the enzyme to improve stability. Hydrophobic interaction by solvents such as MTBE can reduce the amount of bound water molecules on the enzyme. A loss of bound water can cause the protein to fold to a more stable configuration or it may also reduce water dependent reactions such as proteolysis. Hydrogen bonding could not be responsible for improvement in stability since MTBE has no polarized hydrogen bonds necessary for hydrogen bond formation. Pyruvate decarboxylase exhibits good stability to other solvents but inactivates more than the control in each case.

R-PAC production as a function of organic phase solvent

The ability for pyruvate decarboxylase to produce phenylacetyl carbinol (PAC) in a two-phase system was evaluated with each solvent selected above. By evaluating PAC formation with a range of solvents, it may be possible to identify properties of the solvent, which are important for enzyme activity.

PAC production was evaluated with 1.8 M benzaldehyde in the organic solvent phase and 1.43 M pyruvate in the aqueous MOPS phase (2M MOPS, 1 mM TPP, 1 mM $Mg^{2+}$, pH 6.5 at 4° C.). The reaction was started with the addition of enzyme to the aqueous phase at 7.3 U/ml carboligase activity. The volume ratio of organic solvent phase to aqueous phase was maintained at 1. Directly after enzyme addition the reaction was stirred rapidly forming an emulsion to increase reaction rates. After 72 hours a sample was taken from both phases for analysis of pyruvate, benzaldehyde and PAC.

Figure 1B:
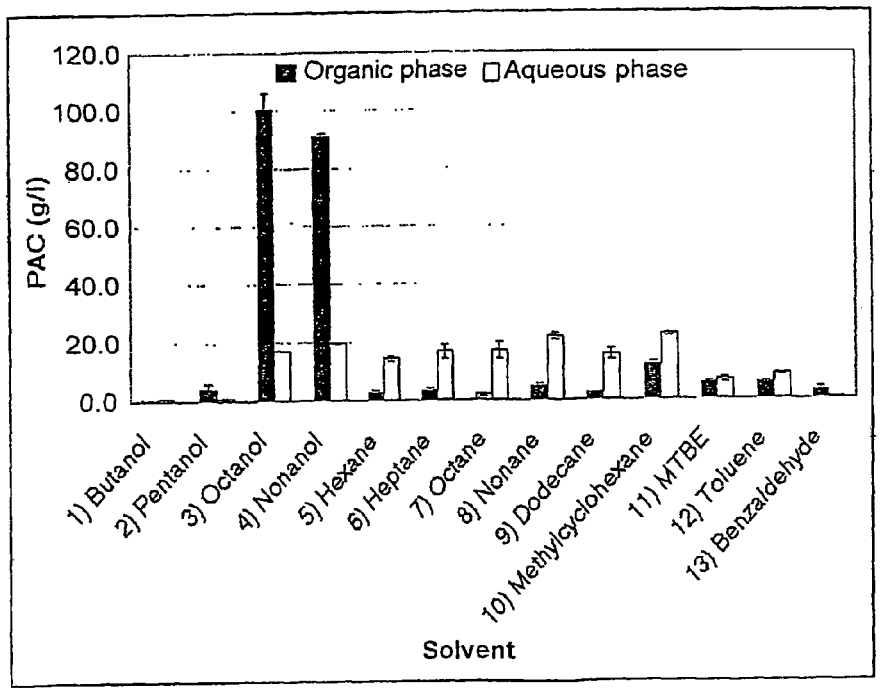

The enzyme produced PAC with each different solvent evaluated. The concentration of PAC in the organic solvent and aqueous phases for each solvent is shown in FIG. 1B. The largest amounts of PAC produced were with octanol and nonanol as organic phase solvents. 100.6 g/l of PAC was measured in the organic phase with an additional 16.9 g/l in the aqueous phase for octanol, and 90.8 g/l in the organic phase and 19.6 g/l in the aqueous phase for nonanol.

The distribution of PAC between the two phases is different for each solvent. FIG. 1B shows that PAC partitions strongly into the organic solvent phase when octanol and nonanol are used. Pentanol and benzaldehyde also cause preferential partitioning of PAC away from the enzyme. Besides log P, the chemical nature of the solvent also plays a role in the distribution of PAC between organic solvent and aqueous phases. Hexane with a log P of 3.5 distributes PAC preferentially to the aqueous phase, while nonanol with a log P of 3.4 distributes PAC strongly to the organic solvent phase. It is unlikely that such a small difference in log P could be responsible for such a dramatic difference in distribution. Alcohols may be a better medium for PAC solubility and extraction from the aqueous phase after enzyme synthesis.

EXAMPLE 2

PAC and Acetoin Production with Varying Enzyme Activity in Two-Phase Separated Mode Variation of enzyme concentration in the two-phase separated mode is directly compared to the two phase-mixed system under the same conditions.

With a volume to surface area ratio of 1.9 cm, 1.08 ml of 1.5M benzaldehyde in octanol was mixed with 1.08 mls of MOPS buffer (2.5M Mops, 1 mM TPP, 1 mM Mg2+ pH 6.5 at 4° C.) containing varying levels of pyruvate decarboxylase from *Candida utilis* and 1.4 M pyruvate. The reactions were stirred slowly with phase separation maintained at 4° C. The reaction was stopped when all of the pyruvate was consumed.

Figure 2:
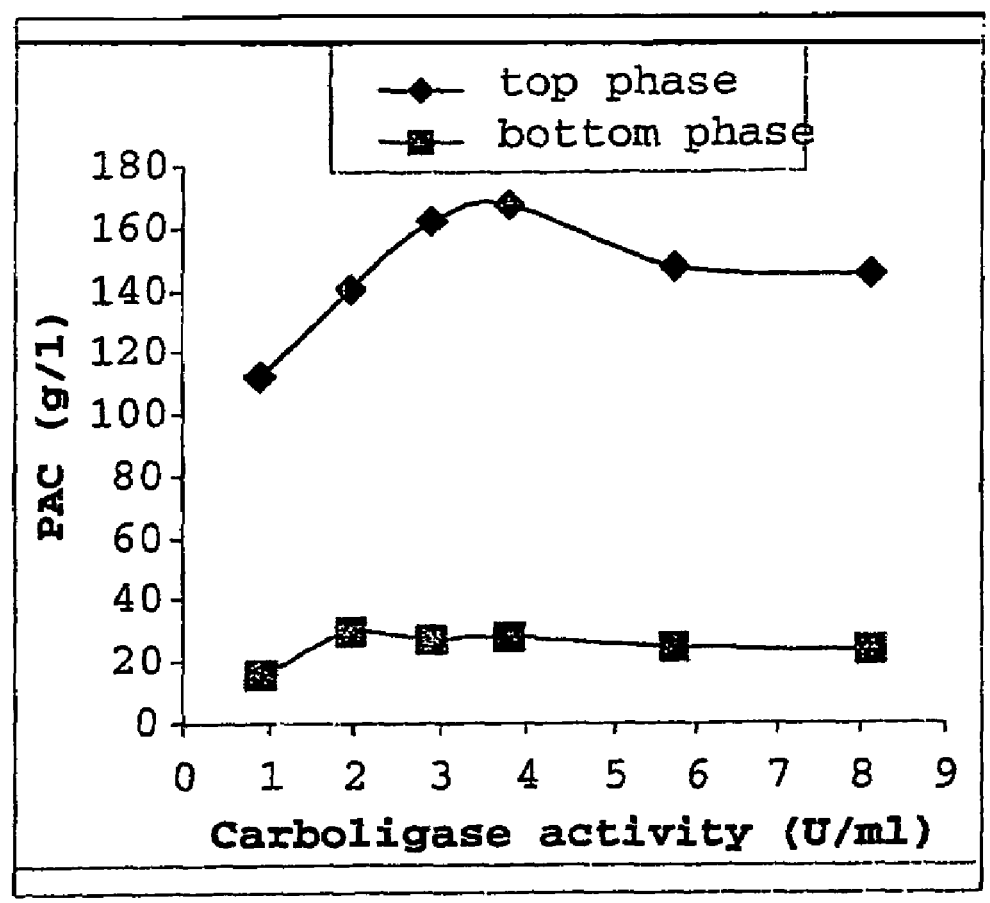
FIG. 2. PAC produced as a function of enzyme activity.

The PAC levels achieved after 395 hours of operation are shown in FIG. 2.

FIG. 2 PAC produced as a function of enzyme activity over 395 hrs at 4° C.

PAC production peaks with 3.8 U/ml of enzyme, achieving 167.3 g/l in the octanol phase and 27.8 g/l in the aqueous phase. This corresponds to 880 g PAC/g PDC based on an assumed specific activity of 17 U/mg protein for purified PDC. The yield of PAC on benzaldehyde was 98% and a yield of PAC on pyruvate is 92.9%. Yields are higher than those achieved in the fully stirred system. Lower losses of pyruvate and benzaldehyde were noted in the control containing no enzyme in comparison to fully stirred operation. Lower losses of substrates could lead to improved yields as these losses are incorporated into the yield calculation.

The final pH rose to 8 in all flasks, which would contribute significantly to enzyme inactivation. Rising pH and substrate limitation could be overcome by scaling up the process, allowing for pH control and substrate feeding.

Tab. 1 shows that the specific production of PAC per amount of enzyme has been increased to 2388 g PAC/g PDC, occurring with 0.9 U/ml activity. At this level of enzyme, 112 g/l PAC is produced in the top phase and 15.6 g/l in the bottom phase.

TABLE 1

Biotransformation final product concentrations, yields and substrate levels for variation of PDC carboligase activity

|  | 0.9 U/ml | 2.0 U/ml | 2.9 U/ml | 3.8 U/ml | 5.8 U/ml |
|---|---|---|---|---|---|
| PAC (g/l) | | | | | |
| Top | 112.2 | 140.6 | 162.0 | 167.3 | 147.2 |
| Bottom | 15.6 | 29.6 | 27.0 | 27.8 | 24.3 |
| g PAC/g PDC | 2388 | 1476 | 1108 | 880 | 508 |
| Benzaldehyde remaining (mM) | 606.6 | 270.9 | 150.9 | 174.3 | 277.2 |
| Pyruvate remaining (mM) | 0 | 0 | 0 | 0 | 0 |
| Yield (PAC/Pyr) % | 60.8 | 81.0 | 87.4 | 92.9 | 81.6 |
| Yield (PAC/Benz) % | 95.3 | 92.3 | 93.3 | 98.0 | 93.4 |
| Acetoin (mM) | | | | | |
| Top | 4.6 | 13.5 | 30.1 | 25.1 | 57.4 |
| Bottom | 6.02 | 17.6 | 20.4 | 33.5 | 28.4 |

Figure 3:
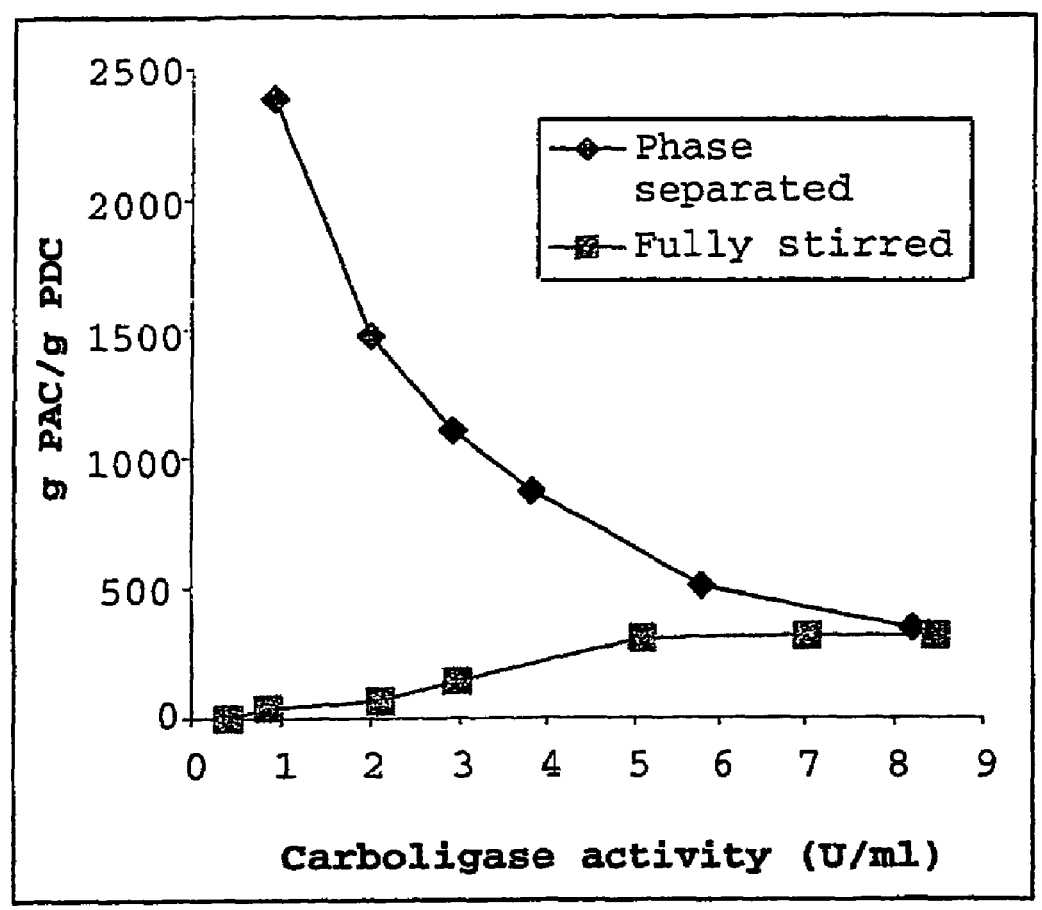
FIG. 3. Comparison of specific PAC production for fully stirred operation and phase-separated operation.

FIG. 3 shows a comparison of specific PAC production for fully stirred operation and phase separated operation. The amount of product per amount of enzyme is significantly increased in phase separated operation.

At this low enzyme level, yields of product on benzaldehyde are high, however yields of product on pyruvate is low at 60.8%. Loss of pyruvate to dimerization could have occurred due to the slow reaction rate and therefore slow pyruvate utilization at this enzyme level. Pyruvate not consumed could be subject to degradation.

FIG. 3 Comparison of the amount of PAC produced per amount of enzyme for phase separated, and fully stirred operation. Both systems started with 1.5M benzaldehyde and 1.4M pyruvate incubated at 4° C. The reaction time for phase separated operation was 395 hrs and 40 hours for fully stirred operation.

EXAMPLE 3

PAC and Acetoin Produced in the Fully Stirred Two Phase System (Mixed Mode)

Separation of acetoin from PAC is necessary for the chemical synthesis of ephedrine. Acetoin shows a negative effect during the reductive amination of R-phenylacetylcarbinol. Therefore minimization of acetoin production and subsequent extraction of acetoin into the aqueous phase away from R-PAC would be beneficial.

Acetoin levels were measured in the two phase-mixed mode in upper octanol phase and lower aqueous phase. Results are shown in Tab. 2. Very low levels of acetoin are produced with this mode of operation in comparison to phase separated operation shown in Tab. 1. This may be due to rapid extraction of acetaldehyde into the upper phase when fully stirred, preventing PDC from catalyzing acetoin formation. Another cause could be increased benzaldehyde delivery to the enzyme favouring PAC over acetoin formation.

TABLE 2

|  | 0.42 U/ml | 0.85 U/ml | 2.11 U/ml | 2.97 U/ml | 5.09 U/ml | 7.03 U/ml | 8.48 U/ml |
|---|---|---|---|---|---|---|---|
| PAC (g/l) | | | | | | | |
| Top | 0 | 1.2 | 6.6 | 22.1 | 81.3 | 115.8 | 142.1 |
| Bottom | 0 | 0.5 | 1.3 | 3.3 | 11.9 | 17.4 | 19.0 |
| g PAC/g PDC | 0 | 34 | 63 | 145 | 311 | 322 | 322 |
| Acetoin (mM) | | | | | | | |
| Top | 1.8 | 0.6 | 1.3 | 0 | 1.4 | 4.7 | 7.2 |
| Bottom | 1.8 | 11.0 | 8.6 | 10.5 | 2.6 | 3.2 | 3.5 |

Figure 4:
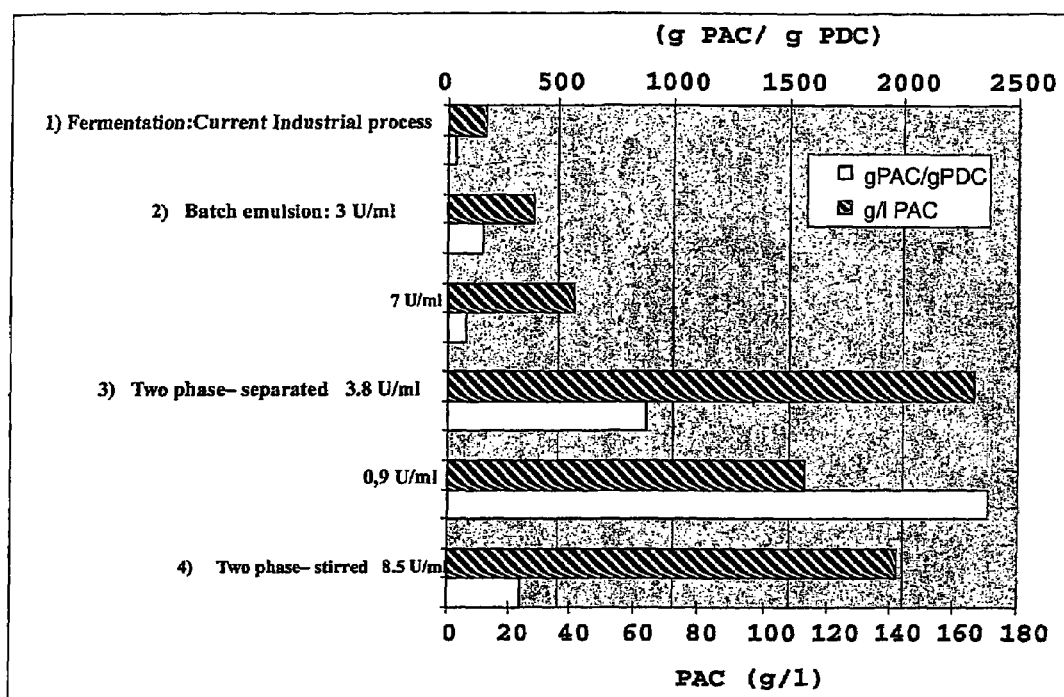
FIG. 4. Productivity of R-phenylacetylcarbinol in different systems.

FIG. 4 R-phenylacetylcarbinol productivity in different systems

EXAMPLE 4

PAC Production from Acetaldehyde and Benzaldehyde in a Two-Phase System

The object of this study is PAC production in an aqueous/organic two-phase system with *Zymomonas mobilis* PDC. Enzyme in the aqueous phase converts substrates benzaldehyde and acetaldehyde delivered from the organic phase. Product PAC is extracted into the organic phase.

4 ml glass vials with screw caps (teflon seals) and a 12 mm magnetic stirrer contained:
  500 μl organic phase, containing 500 mM benzaldehyde and 500 mM acetaldehyde
  400 μl buffer (50 mM MES/KOH pH 7.0, 5 mM $MgSO_4$, 1 mM TPP)

Vials were fully stirred as an emulsion at room temperature (approx. 25° C.) for 30 seconds to allow substrate diffusion into the aqueous phase. After phase separation, the following enzyme preparation was injected into the bottom aqueous phase and stirred rapidly as above.
  100 μl crude extract with *Zymomonas mobilis* PDC-WM in above buffer (final concentration in aqueous phase: PDC activity [aca+bza] 1.58 mM PAC/min; total protein 5 mg/ml)

A control contained substrates in the 400 μl buffer with no organic phase added. Samples were taken after 72 hours and analysed for PAC concentrations in the organic and aqueous phases. For measuring initial substrate concentrations in the aqueous phase, enzyme was replaced by buffer. All experiments were carried out in duplicate.

Figure 5:
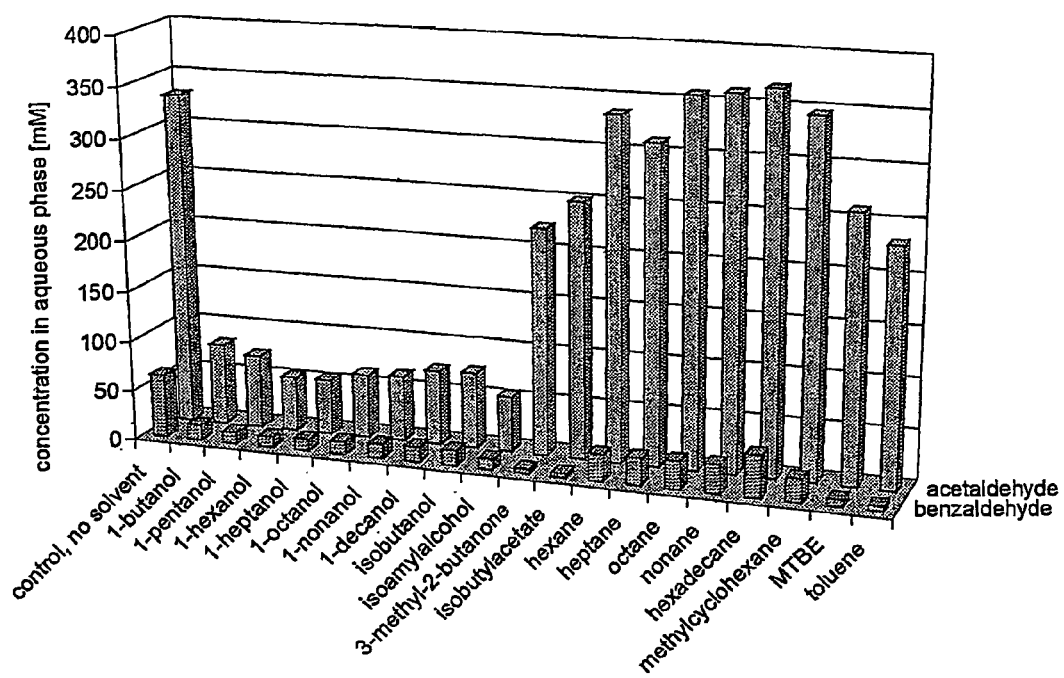
FIG. 5. Showing of initial acetaldehyde concentrations in the aqueous phase.

FIG. 5 shows that with many solvents initial acetaldehyde concentrations in the aqueous phase are higher than 200 mM. These levels would cause strong deactivation of the enzyme. In contrast, acetaldehyde partitions preferentially into the organic phase when alcohols are used, exposing the enzyme to only 54–81 mM acetaldehyde. These are more suitable conditions for the biotransformation. For the alcohols, the concentration of the second substrate benzaldehyde is also low in the aqueous phase (11–15 mM).

Figure 6:
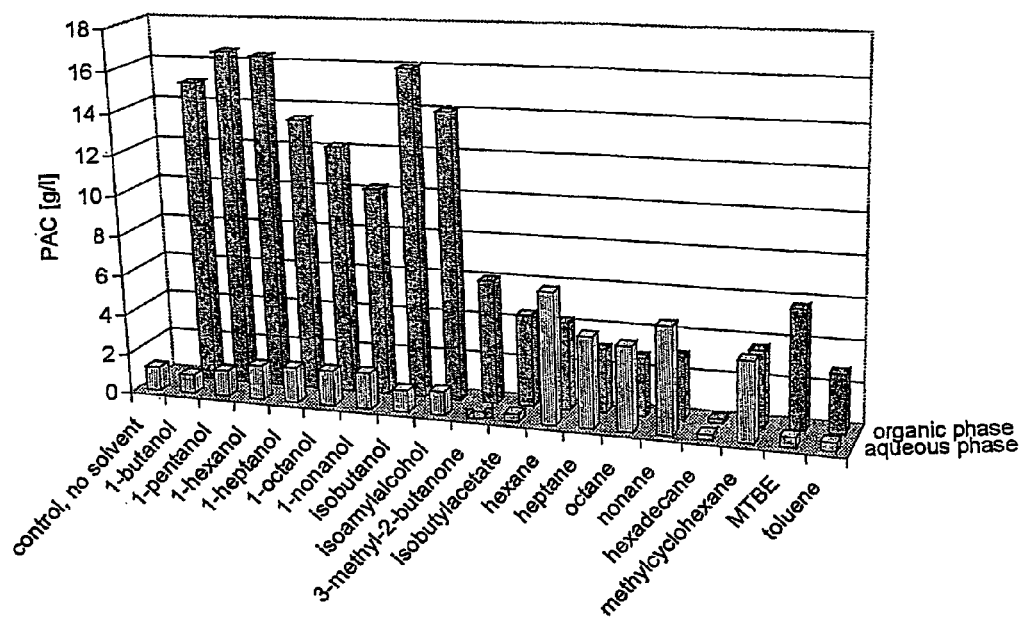

The amount of produced PAC in the various solvent systems is given in FIG. 6. Highest PAC concentrations were achieved with the alcohols 1-pentanol, 1-hexanol and isobutanol (16–16.6 g/l in the organic and 1–1.7 g/l in the aqueous phase). Without the addition of an organic solvent, only 1 g/l PAC was formed. FIG. 2 also shows that PAC preferentially partitioned into the organic phase using the tested alcohols, isobutylacetate, MTBE or toluene, whereas alkanes left most of the PAC produced in the aqueous phase.

Figure 7:
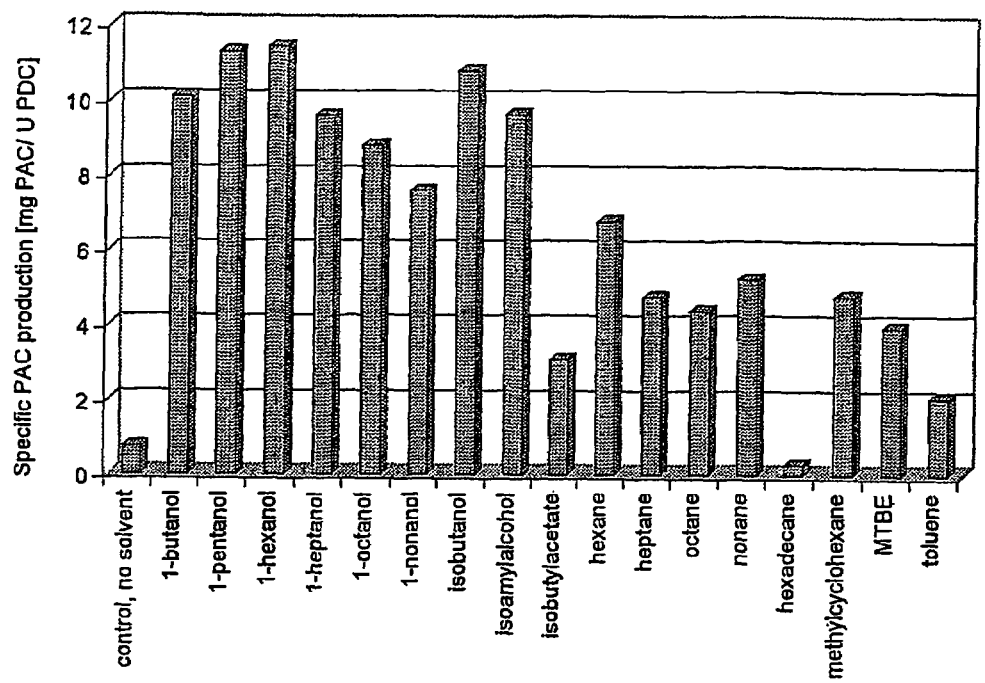

The amount of PAC produced per unit of PDC as shown in FIG. 7 reaches 10.8–11.4 mg/U with 1-pentanol, 1-hexanol and isobutanol as organic phases.

The 8 tested alcohols resulted in best PAC production, lowest acetaldehyde concentration in the aqueous phase and also in the lowest ratio of acetaldehyde to benzaldehyde in the aqueous phase (approximately 5-molar excess). It has been reported, that the ratio acetaldehyde to benzaldehyde is vital for PAC formation with *Zymomonas mobilis* PDC-WM (Iwan et al. J Mol Cat B Enz 11, 2001, 387–396 and Goetz et al. Biotech Bioeng 74, 2001, 317–325). Best results have been achieved for equimolar concentrations of acetaldehyde and benzaldehyde. Therefore the two-phase system might be mainly limited by the unfavourable substrate ratio. This might be overcome by adjusting the substrate ratio in the organic phase or by slow addition of acetaldehyde. The substrate concentrations also need to be in balance with the enzyme activity. Other possible limitations could be acetaldehyde evaporation and enzyme deactivation or inhibition.

FIG. 5: Initital concentrations in the aqueous phase of the two-phase system for PAC production from acetaldehyde and benzaldehyde.

FIG. 6: PAC concentrations after 72 h. 50% vol. solvent (containing 500 mM acetaldehyde and 500 mM benzaldehyde) and 50% vol. aqueous phase were stirred as emulsion at room temperature (approx. 25° C.). The aqueous phase contained 50 mM MES/KOH pH 7.0, 5 mM $MgSO_4$, 1 mM TPP, *Zymomonas mobilis* PDC-WM carboligase activity: 1.58 mM PAC/min (aca+bza), 5 mg protein/ml (1-decanol and n.d.: not determined because the solvents interfered with PAC analysis)

FIG. 7: Specific PAC production with *Zymomonas mobilis* PDC-WM in two-phase system. One unit PDC activity was defined as the amount of enzyme that produced 1 mM PAC per minute from acetaldehyde and benzaldehyde at 25° C. and pH 7.

Other embodiments and advantages of the invention are set forth in part in the description, which follows, and in part, may be obvious from this description, or may be learned from the practice of the invention. All references cited herein, including all U.S. and foreign patents and patent applications, and all publications or other documentary materials, are specifically and entirely hereby incorporated herein by reference. it is intended that the specification and examples be considered exemplary only, with the true scope and spirit of the invention indicated by the following claims.

The invention claimed is:

1. A process for production of phenylacetylcarbinols of formula (I)

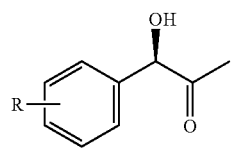

I wherein R is H, F, Cl, or B,
comprising reacting, in a liquid two-phase system, acetaldehyde or pyruvate and an aromatic aldehyde of formula (II)

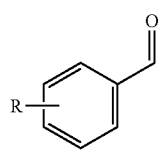

II wherein K is as defined above
in the presence of a private decarboxylase, to form a phenylacetylcarbinol, wherein one phase of the liquid two-phase system is an aqueous phase and the other phase of the liquid two-phase system is an organic phase which comprises an elkanol.

2. The process of claim 1, wherein the organic phase comprises a $C_4$ to $C_{10}$, alkanol.

3. The process of claim 1, further comprising mechanically agitating the two liquid phases of said liquid two-phase system to form an emulsion.

4. The process of claim 1, wherein the pyruvate decarboxylase is derived from a microorganism of the genus *Zymomonas* or *Candida*.

5. The process of claim 1, wherein R═H for the aromatic aldehyde of formula (II).

6. The process of claim 1, further comprising metering the acetaldehyde during the reaction such that acetaldehyde is at a concentration of between 20 and 50 in the aqueous phase.

7. The process of claim 4, wherein the a microorganism is *Candida utilis*.

8. The process of claim 1, wherein the acetaldehyde is reacted with the aromatic aldehyde.

9. The process of claim 1, wherein the pyruvate is reacted with the aromatic aldehyde.

10. The process of claim 1, wherein one liquid phase comprises octanol, nonanol, or octanol and nonanol.

11. The process of claim 1, further comprising mixing the phases of said liquid two-phase system.

12. The process of claim 11, wherein said mixing comprises stirring or shaking such that the two phases are maintained as two discrete phases.

13. The process of claim 11, wherein said mixing comprises stirring or shaking such that the two phases do not exist as separate phases but form an emulsion.

14. The process of claim 4, wherein the microorganism is *Zymbmonas mobilis*.

15. The process of claim 1, further comprising isolating the phenylacetylcarbinol.

16. A method comprising:
reacting acetaldehyde or pyruvate and an aromatic aldehyde of formula (II)

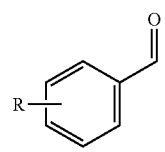

II wherein R is H, F, Cl, or B
in the presence of a pyruvate decarboxylase in a liquid two-phase system wherein one phase of the liquid two-phase system is an aqueous phase and the other phase of the liquid two-phase system is an organic phase which comprises an alkanol;
mixing the two phases of said the liquid two-phase system such that the two phases are maintained as two discrete phases; and
forming a phenylacetylcarbinol of formula (I) wherein R is described as above.

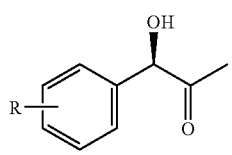
I
17. The method of claim 16, further comprising utilizing the phenylacetylcarbinol as a precursor for production of ephedrine or pseudoephedrine.
18. The method of claim 1, further comprising utilizing the phenylacetylcarbinol as a precursor for production of ephedrine or pseudoephedrine.
* * * * *

UNITED STATES PATENT AND TRADEMARK OFFICE
CERTIFICATE OF CORRECTION

PATENT NO. : 7,074,966 B2
APPLICATION NO. : 10/488202
DATED : July 11, 2006
INVENTOR(S) : Bernhard Hauer et al.

It is certified that error appears in the above-identified patent and that said Letters Patent is hereby corrected as shown below:

On Title Page:

Item (22), PCT Filed, "Sep. 1, 2002" should read -- Aug. 30, 2002 --.

At Column 1, line 7, "Sep. 1, 2002" should read -- Aug. 30, 2002 --.

In Claim 1, at column 7, line 65, "K" should be changed to --R--; at column 8, line 3, "elkanol" should read --alkanol--.

In Claim 2, at column 8, line 6, "$C_{10}$," should read --$C_{10}$--.

In Claim 6, at column 8, line 19, "50" should read --50 mMol/L--.

In Claim 14, at column 8, line 39, "*Zymbmonas*" should read --*Zymomonas*--.

In Claim 16, at column 8, line 62, "of said the" should read --of the--.

Signed and Sealed this

Twenty-sixth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,074,966 B2
APPLICATION NO. : 10/488202
DATED : July 11, 2006
INVENTOR(S) : Bernhard Hauer et al.

It is certified that error appears in the above-identified patent and that said Letters Patent is hereby corrected as shown below:

On Title Page:

Item (22), PCT Filed, "Sep. 1, 2002" should read --Aug. 30, 2002--.

At Column 1, line 7, "Sep. 1, 2002" should read --Aug. 30, 2002--.

In Claim 1, at column 7, line 65, "K" should be changed to --R--; at column 8, line 3, "elkanol" should read --alkanol--.

In Claim 2, at column 8, line 6, "$C_{10}$," should read --$C_{10}$--.

In Claim 6, at column 8, line 19, "50" should read --50 mMol/L--.

In Claim 14, at column 8, line 39, "*Zymbmonas*" should read --*Zymomonas*--.

In Claim 16, at column 8, line 62, "of said the" should read --of the--.

This certificate supersedes the Certificate of Correction issued December 26, 2006.

Signed and Sealed this

Fourth Day of August, 2009

JOHN DOLL
*Acting Director of the United States Patent and Trademark Office*